US012636155B2

(12) United States Patent     (10) Patent No.:   US 12,636,155 B2

Sengun et al.     (45) Date of Patent:    May 26, 2026

---

(54) SOFT GLENOID AWNING AND RELATED REPAIR PROCEDURES

(71) Applicant: Medos International Sarl, Le Locle (CH)

(72) Inventors: Mehmet Ziya Sengun, Canton, MA (US); Stefan Gabriel, Raynham, MA (US); Gerome O. Miller, Randolph, MA (US)

(73) Assignee: Medos International Sàrl, Le Locle (CH)

( * ) Notice: Subject to any disclaimer, the term of this patent is extended or adjusted under 35 U.S.C. 154(b) by 537 days.

(21) Appl. No.: 18/098,452

(22) Filed: Jan. 18, 2023

(65) Prior Publication Data

US 2023/0329869 A1     Oct. 19, 2023

Related U.S. Application Data

(62) Division of application No. 16/781,094, filed on Feb. 4, 2020, now Pat. No. 11,559,402.

(51) Int. Cl.
   *A61F 2/40*       (2006.01)
   *A61F 2/30*       (2006.01)
           (Continued)

(52) U.S. Cl.
   CPC ...... *A61F 2/30721* (2013.01); *A61F 2/30749* (2013.01); *A61F 2/4081* (2013.01); 
           (Continued)

(58) Field of Classification Search
   CPC ... A61F 2/4081; A61F 2/4612; A61F 2/30756
   See application file for complete search history.

(56) References Cited

U.S. PATENT DOCUMENTS 7,204,839 B2    4/2007   Dreyfuss et al.
8,894,713 B2   11/2014   Shohat et al.
       (Continued)

FOREIGN PATENT DOCUMENTS

CN       1925814 A     3/2007

OTHER PUBLICATIONS

Extended European Search Report for Application No. 21155005.8, issued Jun. 17, 2021 (8 pages).
       (Continued)

*Primary Examiner* — Brian A Dukert

(74) *Attorney, Agent, or Firm* — Barnes & Thornburg LLP

(57)        ABSTRACT

Systems and methods for opposing abnormal motion of an adjacent bone are provided. One exemplary embodiment of a surgical method includes delivering and securing a bone barrier to a bone bed of a glenoid such that at least a portion of the bone barrier extends laterally beyond the bone bed and can oppose, prevent, and/or reduce abnormal motion of an adjacent bone (e.g., a humeral head). The bone barrier can be secured along a periphery of a glenoid of a shoulder. More particularly, the bone barrier can be placed and secured such that at least a portion of the bone barrier extends laterally over the glenoid and can oppose abnormal motion of the humeral head. In some embodiments at least one suture anchor and suture can secure the bone barrier to the bone bed.

17 Claims, 7 Drawing Sheets

(51) Int. Cl.
    *A61F 2/46*         (2006.01)
    *A61B 17/04*      (2006.01)

(52) U.S. Cl.
    CPC ........ *A61F 2/4612* (2013.01); *A61B 17/0401*
    (2013.01); *A61F 2002/30461* (2013.01); *A61F*
    *2002/30754* (2013.01); *A61F 2002/4635*
    (2013.01)

(56) References Cited

U.S. PATENT DOCUMENTS

| | | |
|---|---|---|
| 8,900,320 B2 | 12/2014 | Frederick et al. |
| 9,314,339 B2 | 4/2016 | Mansmann |
| 9,345,567 B2 | 5/2016 | Sengun |
| 9,463,010 B2 | 10/2016 | Gittings et al. |
| 9,504,577 B2 | 11/2016 | Frederick et al. |
| 9,549,820 B2 | 1/2017 | Mroczkowski et al. |
| 11,559,402 B2 | 1/2023 | Sengun et al. |
| 2004/0133276 A1 | 7/2004 | Lang et al. |
| 2007/0179624 A1 | 8/2007 | Stone et al. |
| 2007/0293947 A1 | 12/2007 | Mansmann |
| 2012/0109328 A1 | 5/2012 | Meridew |
| 2012/0109331 A1 | 5/2012 | Meridew et al. |
| 2013/0116794 A1 | 5/2013 | Shohat et al. |
| 2014/0257499 A1 | 9/2014 | Winslow et al. |
| 2015/0157462 A1 | 6/2015 | Ek et al. |
| 2017/0027708 A1 | 2/2017 | Shenoy |
| 2017/0095324 A1 | 4/2017 | Adams et al. |
| 2017/0112625 A1* | 4/2017 | Taverna ............. A61B 17/1778 |
| 2017/0215864 A1 | 8/2017 | Sengun et al. |
| 2017/0216015 A1 | 8/2017 | Sengun et al. |
| 2017/0273680 A1 | 9/2017 | Sengun et al. |
| 2021/0045886 A1* | 2/2021 | Maiotti ................. A61F 2/4059 |
| 2021/0236289 A1 | 8/2021 | Sengun et al. |

OTHER PUBLICATIONS

Chinese Office Action for Application No. 202110166540.7 issued Apr. 27, 2025 (13 pages).
Japanese Notice of Reasons for Refusal for Application No. 2021-015538 dated Jul. 15, 2025 (13 pages).

* cited by examiner

SOFT GLENOID AWNING AND RELATED REPAIR PROCEDURES

CROSS REFERENCE TO RELATED APPLICATIONS

The present application is a divisional of and claims priority to U.S. patent application Ser. No. 16/781,094, filed Feb. 4, 2020, the content of which is hereby incorporated by reference in its entirety.

FIELD

The present disclosure relates to systems, devices, and methods for preventing excessive bone migration in a shoulder with a damaged rotator cuff, and more particularly relates to a bone barrier, and associated components, for implantation into a shoulder with an irreparable rotator cuff, as well as surgical methods of implanting the same.

BACKGROUND

The shoulder is made up of two joints, the acromioclavicular joint (AC joint) and the glenohumeral joint. The glenohumeral joint (i.e., the "ball-and-socket" joint) is where the humerus bone head (the ball) and the glenoid (the socket) meet. The glenoid is rimmed with soft tissue, the labrum, which makes a deeper socket and molds to fit the humeral head. The AC joint is where the acromion, the scapula (shoulder blade) and the clavicle meet. The rotator cuff spans the glenohumeral joint and connects the humerus to the scapula. Muscles of the rotator cuff keep the humerus tightly in the socket, while tendons of the rotator cuff attach the muscle to bone.

A torn rotator cuff is a common shoulder injury, particularly among athletes, which can result in pain, weakness, and a limited range of motion. In some cases, rest, ice, and physical therapy can be sufficient for recovery from a rotator cuff injury. Other times, surgery can be required to repair a torn rotator cuff. With some injuries, however, a torn rotator cuff may be irreparable. In some cases, an irreparable rotator cuff can no longer keep the humeral head tightly in the socket of the glenoid, and a fulcrum of the humeral head may become unstable. This instability can lead to excessive migration of the humeral head causing shoulder dysfunction, and possibly, pseudo-paralysis of the shoulder.

In current practice, one solution to the problem of an irreparable rotator cuff injury is a reverse total reconstruction of the shoulder in which the anatomy of the ball-and-socket shoulder joint is reversed. In the reverse total reconstruction an artificial shoulder joint is surgically implanted into a patient's shoulder, with the ball part of the shoulder joint implanted onto the shoulder blade and the socket portion of the shoulder joint implanted onto the humeral head. This procedure is very intrusive and still has an unknown long-term outcome.

Another approach is a superior capsule reconstruction. In a superior capsule reconstruction, a graft can be fixated and spanned between the glenoid and the greater tubercle of the humerus. This procedure can be difficult and time consuming to perform. An additional alternative approach to an irreparable rotator cuff injury can include placing a biodegradable spacer between the humeral head and the coraco-acromial arch. With this approach, the biodegradable spacer is not fixated to the body. This can result in spacer dislocation that requires removal. Furthermore, the biodegradable spacer may lose integrity within a year, and longer-term effects are not well-known.

Accordingly, there is a need for systems, devices, and methods that provide a less intrusive, less time consuming, less burdensome, and more reliable long-term solution to prevent subluxation of a humeral head in a shoulder joint with a damaged rotator cuff.

SUMMARY

The systems, devices, and methods described herein generally relate to implanting a bone barrier in a shoulder joint to prevent abnormal bone movement and/or maintain normal motion. The bone barrier can be secured to a bone bed of a glenoid to prevent excessive humeral head migration. In situations in which a rotator cuff is irreparable, the bone barrier can prevent abnormal humeral head motion while maintaining normal motion of the humerus. The bone barrier can be secured such that a terminal end of the bone barrier extends laterally over a terminal end of the bone bed of the glenoid. In other words, the bone barrier can form an "awning" over a portion of the glenoid to prevent abnormal humeral head motion.

One exemplary embodiment of a surgical method includes delivering a bone barrier to a bone bed of a glenoid such that a distal-facing surface of the bone barrier is fixed relative to the glenoid, including at least a portion of the bone bed, and a terminal end of the bone barrier extends laterally beyond a terminal end of the bone bed. The method includes securing the bone barrier to the glenoid such that normal motion of an adjacent humeral head is unimpeded by the bone barrier.

Delivering the bone barrier can include arthroscopically delivering the bone barrier. In some embodiments, the bone bed can be located near a labrum of the glenoid. Securing the bone barrier to the bone bed can further include securing the bone barrier such that a terminal end of the bone barrier forms an awning over a labrum and/or a rim of the glenoid. Securing the bone barrier can include securing the bone barrier such that a terminal end of the bone barrier extends laterally over a terminal end of the bone bed. Securing the bone barrier to the bone bed can include driving a screw through the bone barrier and into the bone bed. Securing can further include doing so with a washer. In some such embodiments, the screw can enter the bone bed at a location near a rim of the glenoid. Securing the bone barrier to the bone bed can include using at least one staple extending through the bone barrier into the bone bed.

Another exemplary surgical method includes identifying a suitable bone bed at a location opposing abnormal migration of a bone and preparing the bone bed for receiving a bone barrier. The method also includes fixing the bone barrier to the bone bed using at least one suture anchor such that abnormal migration of the bone is prevented.

Fixing the bone barrier to the bone can include fixing the bone barrier such that a terminal end of the bone barrier extends laterally over a terminal end of the bone bed. Alternatively, or additionally, fixing the bone barrier to the bone bed using the at least one suture anchor can further include inserting the at least one suture anchor into the bone bed, passing at least one suture through the suture anchor and the bone barrier, reducing the bone barrier to the bone bed, and securing the bone barrier to the bone bed. Inserting the at least one suture anchor into the bone can include inserting the at least one suture anchor near a rim of a glenoid. In some embodiments, passing the at least one suture through the suture anchor and the bone barrier can include passing at least one suture limb of the suture under or through a labrum of the glenoid prior to passing the at least one suture limb through the bone barrier. Alternatively, passing the at least one suture through the suture anchor and the bone barrier can include passing at least one suture limb of the suture under or through a labrum of the glenoid after passing the at least one suture limb through the bone barrier. In other embodiments, passing the at least one suture through the suture anchor and the bone barrier can include passing at least one suture limb of the at least one suture through the bone barrier, connecting the at least one suture limb to a mating limb of the at least one suture, and tying a sliding knot with the at least one suture limb and the mating limb at a location proximal to the bone barrier. Reducing the bone barrier to the bone bed can include passing the bone barrier through a cannula to the bone bed. Securing the bone barrier to the bone bed can include tying at least one half-hitch in the at least one suture.

In some embodiments, fixing the bone barrier can prevent abnormal migration of a humeral head. The bone barrier can include a plurality of discrete bone barriers, and fixing the bone barrier can further include independently fixing each of the plurality of discrete bone barriers.

In one exemplary embodiment a system for preventing bone migration comprises a bone barrier that includes a strong, conforming material that conforms to a portion of a bone bed of a glenoid and to a portion of the glenoid adjacent to the bone bed. The bone barrier is dimensioned such that it contacts an adjacent humeral head to maintain desired motion of the humeral head with respect to the glenoid and to prevent abnormal migration of the humeral head with respect to the glenoid. The system also includes one or more securing means for attaching the bone barrier to the glenoid such that a terminal end of the bone barrier extends laterally beyond a terminal end of the bone bed.

In some embodiments the bone bed can be located along a periphery of the glenoid. The bone barrier can be formed from a biological material suitable for long term placement within a body. In some embodiments the bone barrier can include a fibrous tissue. In other embodiments the bone barrier can include a synthetic material. The bone barrier can include two or more distinct materials. Alternatively, or additionally, the bone barrier can include two or more discrete buffer pieces.

The securing means can include at least one suture anchor and at least one suture. In some embodiments, the securing means can include at least one screw and at least one washer. In other embodiments, the securing means can include at least one staple.

BRIEF DESCRIPTION OF DRAWINGS

This disclosure will be more fully understood from the following detailed description taken in conjunction with the accompanying drawings, in which.

DETAILED DESCRIPTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present disclosure is defined solely by the claims. The features illustrated or described in connection with one exemplary embodiment may be combined with the features of other embodiments. Such modifications and variations are intended to be included within the scope of the present disclosure. While a bone barrier disclosed herein is discussed primarily in relation to a shoulder/glenoid of a human, it will be appreciated that the bone barrier of the present disclosure can be applied to equivalent anatomies in other animals and/or to other anatomies in a body of a human or other animal.

The figures provided herein are not necessarily to scale, although a person skilled in the art will recognize instances where the figures are to scale and/or what a typical size is when the drawings are not to scale. While in some embodiments movement of one component is described with respect to another, a person skilled in the art will recognize that other movements are possible. To the extent features or steps are described herein as being a "first feature" or "first step," or a "second feature" or "second step," such numerical ordering is generally arbitrary, and thus such numbering can be interchangeable. Moreover, a person skilled in the art will appreciate that not all of the method steps disclosed herein are required, and, in view of the present disclosure, will understand how modifications can be made to each step, the order of the steps, the limitation of certain steps, etc. without departing from the spirit of the present disclosure while still achieve the desired goals, including, for example, securing a bone barrier to a glenoid to oppose abnormal motion and/or maintain normal motion of surrounding bones (e.g., a humeral head). Additionally, a number of terms may be used throughout the disclosure interchangeably but will be understood by a person skilled in the art. By way of non-limiting example, the terms "suture" and "filament" may be used interchangeably, and in some instances, simultaneously.

Figure 1:
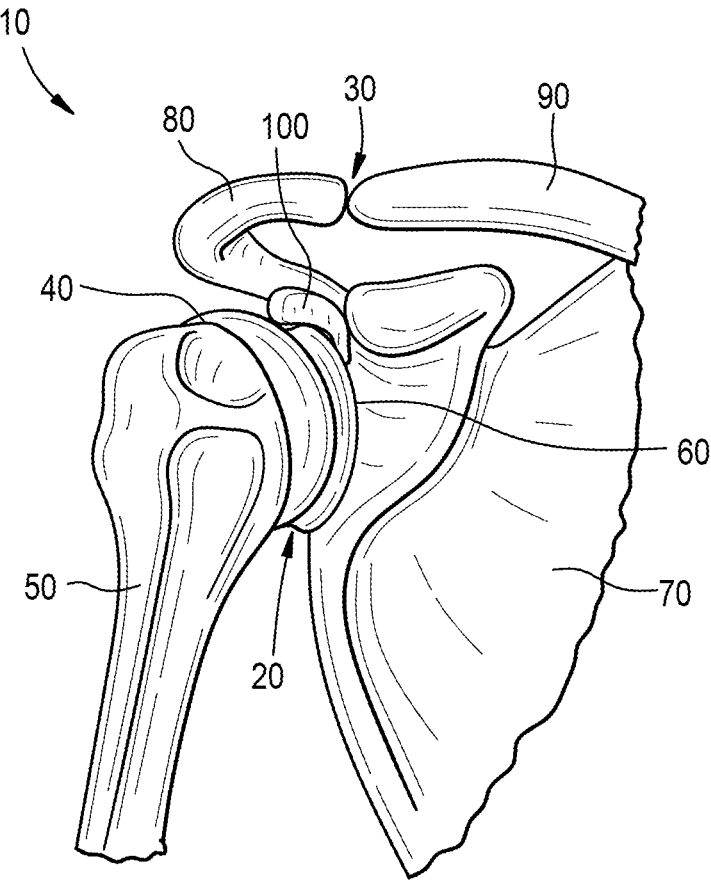
FIG. 1 is a front view of a shoulder joint having one exemplary embodiment of a bone barrier located therein.
Figure 2:
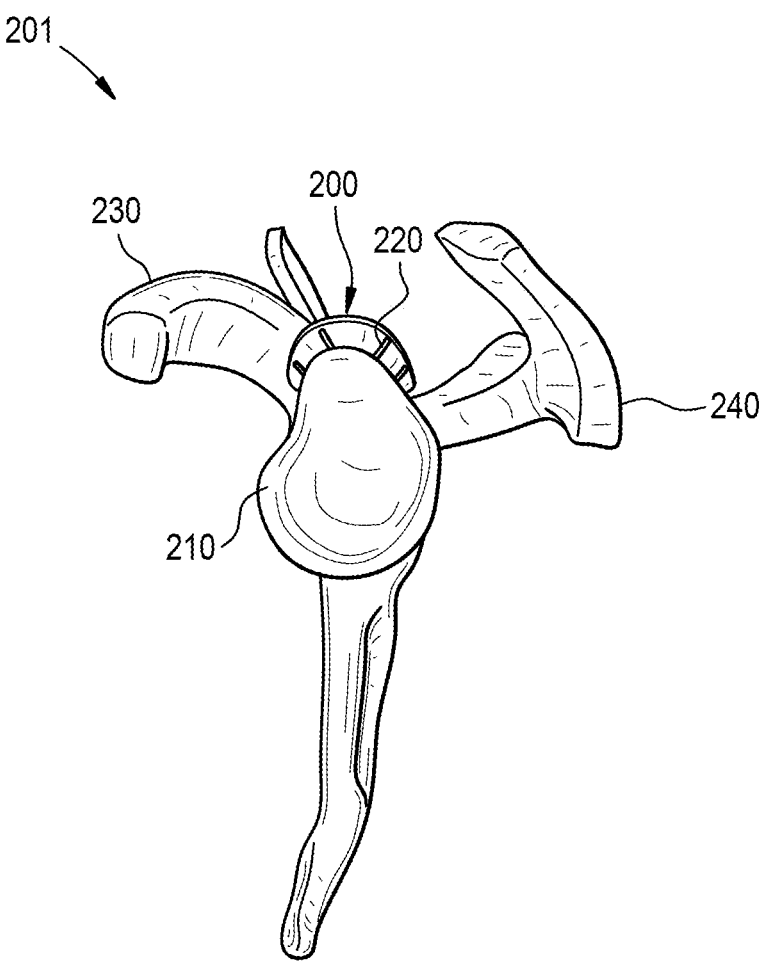
FIG. 2 is a front view of a shoulder joint having another exemplary embodiment of a bone barrier located therein.
Figure 3:
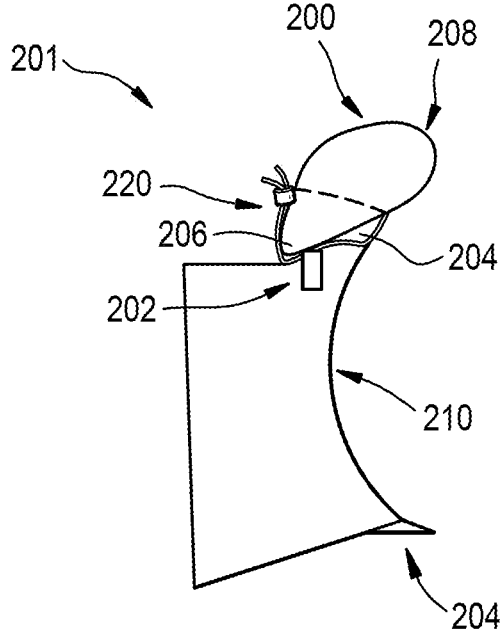
FIG. 3 is a schematic side view of the shoulder joint with the bone barrier located therein of FIG. 2.

The present disclosure is directed to systems, devices, and methods for preventing subluxation of a humeral head, for example, in the case of an irreparable rotator cuff. In one embodiment, an appropriately sized bone barrier or soft awning can be attached in one or more strategic location(s) around a glenoid to diminish excessive migration of the humeral head. FIGS. 1-3 illustrate non-limiting exemplary embodiments of a bone barrier of the present disclosure surgically implanted within a shoulder of a patient. FIG. 1 illustrates the anatomy of a shoulder 10 with a strategically placed bone barrier 100. The shoulder 10 has two joints—a glenohumeral joint 20 and an acromioclavicular (AC) joint 30. The glenohumeral joint 20 is where a humeral head 40 of the humerus 50 joins with a glenoid surface 60. The AC joint 30 is where a scapula, i.e., a shoulder blade 70, an acromion bone 80, and a clavicle 90 join. In one embodiment, a bone barrier 100 can be placed strategically along a periphery of the glenoid 60 to oppose abnormal migration of the humeral head 40. Abnormal migration can also include anticipated abnormal migration and/or possible abnormal migration. In other words, the bone barrier 100 can be placed strategically to preemptively prevent, reduce, or oppose abnormal migration of the humeral head 40 in the future. More particularly, in some embodiments, the bone barrier can be configured to prevent partial dislocation or subluxation of the humeral head. In some embodiments, the bone barrier can be secured to a bone or bone bed (e.g., a glenoid) to form a soft awning to prevent and/or oppose abnormal migration of the humeral head. A bone barrier of the present disclosure can, additionally or alternatively, maintain a desired motion. Desired motion can be normal, typical motion of the humeral head, or other bone if the bone barrier is used in a location other than the shoulder/glenoid. A person skilled in the art will appreciate that normal, typical motion of the humeral head includes, but is not limited to, approximately 180 degrees in flexion, approximately in the range of about 45 degrees to about 60 degrees in extension, approximately in the range of about 70 degrees to about 90 degrees for internal rotation, approximately about 90 degrees for external rotation, the ability to achieve adduction, the ability to achieve abduction (with a normal range of motion of about 150 degrees), and other motions provided for herein or otherwise known in the art. Likewise, a person skilled in the art will appreciate that abnormal migration or motion includes, but is not limited to, translation of a humeral head beyond its normal range of motion (e.g., upwards, anterior, and/or posterior translations, or a combination thereof, beyond the normal range of motion of the humeral head), and other motions provided for herein or otherwise known in the art.

FIG. 2 illustrates a shoulder 201 with a bone barrier 200 of the present disclosure that can be strategically placed to oppose abnormal motion and/or maintain normal motion of a humeral head. For example, as illustrated in FIG. 2, the bone barrier 200 can be placed along a periphery of a glenoid 210 to oppose abnormal upwards migration of a humeral head. As discussed above, the placement of the bone barrier 200 to oppose abnormal migration or movement can also include anticipated or possible abnormal migration or movement. Accordingly, in some embodiments, the bone barrier 200 can be placed preemptively to prevent, reduce, or oppose abnormal migration of the humeral head in the future. As will be discussed in detail below, the bone barrier can be secured to a bone bed of the glenoid 210. The bone bed, for example, can be located adjacent to the glenoid and/or located at or near a rim of the glenoid 210. In instances in which a labrum of the glenoid 210 is intact, the bone bed can be located near the labrum of the glenoid.

The present disclosure provides for a variety of ways by which the various bone barriers disclosed herein (e.g., bone barrier 200) can be secured at desired location with respect to the glenoid. By way of non-limiting example, the bone barrier 200 can be attached to the bone bed by one or more sutures or tethers 220. While the illustrated configuration of FIG. 2 includes four sutures 220, it will be appreciated that a greater or fewer number of sutures 220 can be used to secure the bone barrier 200 to the bone bed. Likewise, other constructs besides sutures can be used to form a tether between the barrier and the bone. In one embodiment, the bone barrier 200 can be placed along an upper periphery of the glenoid 210. With such a placement, the bone barrier 200 can oppose abnormal upwards translation of a humeral head (i.e., upwards translation of the humeral head beyond a natural range of motion). The bone barrier 200 can act to prevent the humeral head from moving upwards towards other parts of the shoulder anatomy 201, such as, for example, an acromion bone 240.

FIG. 3 shows a schematic side view of the shoulder joint 201 of FIG. 2 with the bone barrier 200 attached to a bone bed of the glenoid 210. In one embodiment, at least one suture anchor 202 can be implanted into the glenoid 210, and, more particularly, into a bone bed of the glenoid 210. A distal-facing surface 206 of the bone barrier 200 can contact the bone bed of the glenoid 210. More particularly, the bone barrier 200 can be delivered and secured to the bone bed of the glenoid 210 such that a distal facing surface 206 of the bone barrier 200 can be fixed relative to, and/or be in contact with, the bone bed. At least one suture 220 can be passed through the suture anchor 202 and the bone barrier 200 to secure the bone barrier to the glenoid 210. By way of non-limiting example, the suture anchor 202 can be implanted into the bone bed of the glenoid 210 at a location just behind a labrum 204 of the glenoid 210. The labrum 204 forms a rim around the glenoid 210. It will be appreciated that a position of the at least one suture anchor can be a function of, among other factors, a desired bone barrier size and orientation as defined by patient-specific and/or procedure-specific needs.

In some embodiments, the bone barrier 200 can oppose abnormal motion and/or maintain normal motion of a humeral head by forming an awning over the glenoid 210. A terminal end 208 of the bone barrier 200 can extend laterally beyond a terminal end of the bone bed of the glenoid 210 such that the bone barrier 200 forms an awning or overhang over the glenoid 210. The awning of the bone barrier 200 can extend over the labrum and/or a bone rim of the glenoid 210. In this manner, the awning of the bone barrier 200 can oppose or prevent abnormal motion, such as, for example, abnormal upwards translation of the humeral head beyond a natural range of motion towards other bones of the shoulder 201, while maintaining a natural range of motion of the humeral head and humerus.

A bone barrier of the present disclosure can be made from a strong, conforming material. The material of the bone barrier can be selected such that the bone barrier does not over-constrain normal motion of a humeral head and does not damage the humeral head upon repeated contact. The material can be natural or artificial. A biological graft can advantageously allow for remodeling and can be incorporated into the body for long term benefits. By way of non-limiting example, exemplary materials include strong fibrous tissue, e.g., a ligament, tendon allograft, autograft, etc., or a synthetic material. In some embodiments, the bone barrier can be made from a single material, while in other embodiments the bone barrier can include two or more materials. For example, the bone barrier can have a relatively hard and/or stiff core covered by a compliant surface material, such as, for example, a bone core covered by periosteum.

A shape and size/dimensions of a bone barrier can be selected, at least in part, based on particular circumstances surrounding a procedure such that the bone barrier effectively opposes abnormal humeral head motion. Exemplary shapes can include a crescent-shape, as shown for example in FIGS. 1 and 2, among others, and the shape can be formed on a patient-by-patient basis to allow for conformability to a patient's individual anatomy.

Dimensions and/or size of the bone barrier, like shapes, can also be formed on a patient-by-patient basis. Factors that may impact the shape and/or dimensions of the bone barrier (s) include but are not limited specific patient needs, anatomical structure, surgical procedure requirements, surgical procedure constraints, and/or surgeon preference(s). By way of non-limiting examples, a surface area of a surface of the bone barrier that is configured to contact the bone surface (e.g., the distal-facing surface 206 of FIGS. 2 and 3) onto which the barrier is being attached (e.g., the glenoid rim) and extend laterally beyond the terminal end of the bone bed (i.e., the "awning") can be approximately in the range of about 50 millimeters$^2$ to about 1000 millimeters$^2$, and a thickness t (see FIG. 3) of the barrier can be approximately in the range of about 1 millimeter to about 20 millimeters at a thickest portion, recognizing the thickness can, but does not have to, change across a length and/or width of the bone barrier. A person skilled in the art will appreciate many other sizes and shapes that the bone barrier(s) can have without departing from the spirit of the present disclosure.

By allowing the shapes and sizes of the bone barriers to be tailored for an individual patient, an appropriately sized and shaped bone barrier can be used in a given procedure to cater to a specific circumstance of a patient and prevent abnormal movement of surrounding bone(s). The tailoring can be done ahead of time, for instance by creating pre-made bone barriers sized and shaped for typical patient anatomies (i.e., mass-produced "typical" bone barriers based on known typical patient anatomies) or based on measurements provided to a manufacturer of an individually-tailored bone barrier, or on-site, such as using a three-dimensional printer or forming a graft of a desired size and shape based on measurements taken at the surgical site in real time or near real time (i.e., close to a time of when the surgery is performed).

In some embodiments, a bone barrier can be a single continuous piece of material. For example, as shown in FIG. 3, the bone barrier 200 can be a single component made from a strong, conformable material. As can be seen, the bone barrier 200 can be secured to the glenoid 210 without a separate base or distinct anchoring portion on the bone barrier itself. In other embodiments, a bone barrier can be formed of multiple discrete pieces.

FIGS. 4-9 illustrate steps or actions in an exemplary method of securing a bone barrier of the present disclosure to a bone bed of a glenoid. The bone barrier can be attached and secured relative to a bone (e.g., a bone bed of a glenoid) such that abnormal motion of an adjacent bone (e.g., a humeral head) can be prevented or reduced. As will be described in detail below, an exemplary method can include preparing a bone bed, inserting a suture anchor(s) into the bone bed, passing a suture(s) through the suture anchor(s) and a bone barrier(s), reducing the bone barrier(s) to the bone bed, and securing a location of the bone barrier(s) with respect to the bone bed such that abnormal motion of an adjacent bone(s) can be prevented and/or reduced (e.g., tying at least one knot in the suture(s)). As illustrated in FIGS. 4-9, a labrum of a patient can remain intact. In instances in which a labrum of a patient is not intact, a labrum implant or artificial labrum can be surgically inserted and attached to replace the labrum.

Figures 4, 5, 6:
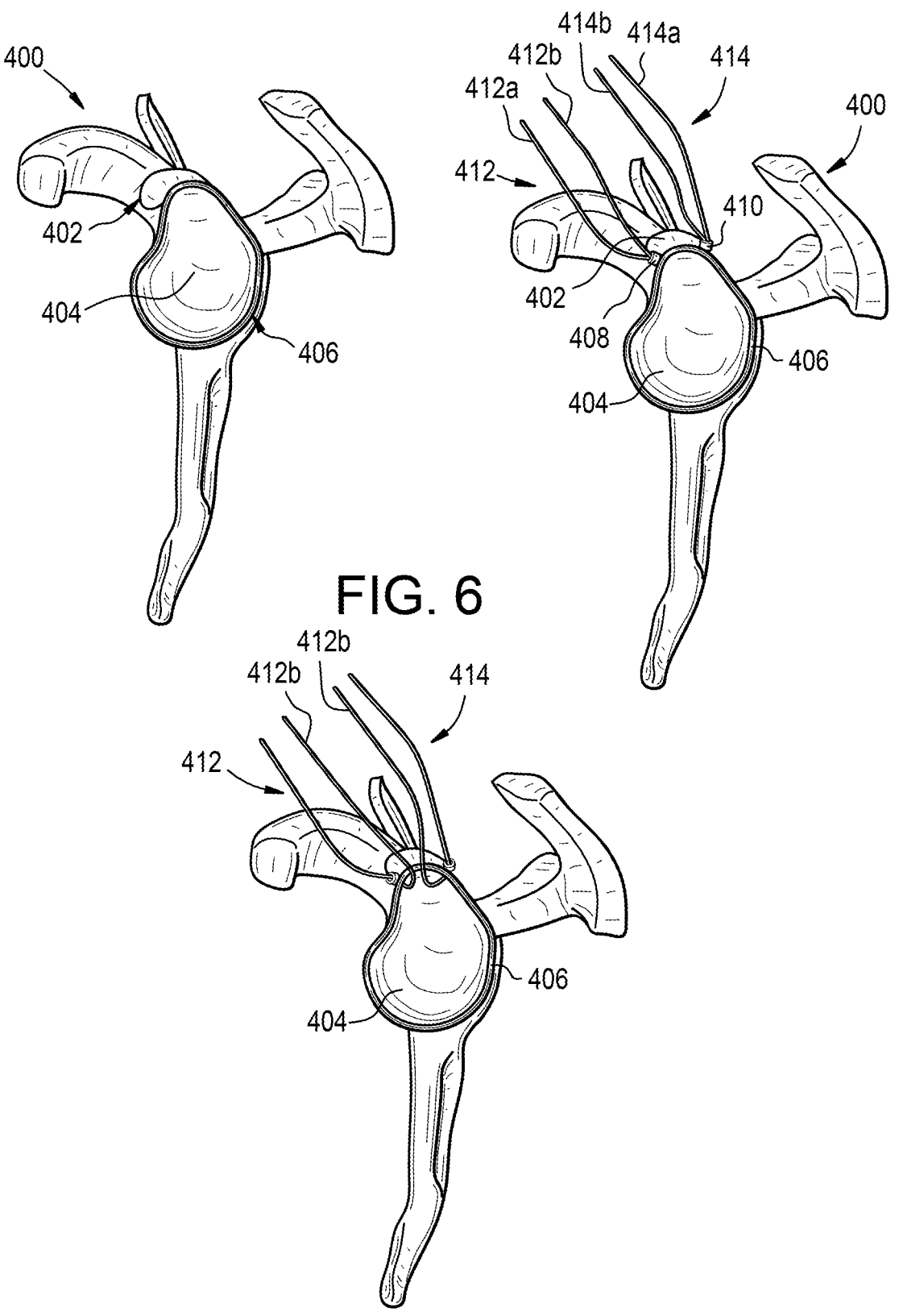
FIG. 4 is a front view of a shoulder joint illustrating a portion of one exemplary method of implanting a bone barrier (not shown until FIG. 7) on a glenoid.
FIG. 5 is a front view of the shoulder joint of FIG. 4 illustrating a second portion of the one exemplary method started in FIG. 4, including the addition of sutures.
FIG. 6 is a front view of the shoulder joint of FIG. 4 illustrating a third portion of the one exemplary method started in FIG. 4.

FIG. 4 illustrates a first step of an exemplary method, which can include preparing a bone bed 402 of a shoulder 400 for receiving a bone barrier. More particularly, tissue can be cleaned away to reach the bone bed 402 of the shoulder 400. A location of the bone bed 402 can be selected such that a bone barrier can be received and secured thereon to oppose abnormal upwards motion of a humeral head. By way of non-limiting example, the bone bed 402 can be located on a periphery of a glenoid 404 of the shoulder 400. In cases in which a labrum 406 of the glenoid 404 remains intact, the bone bed 402 can be located near the labrum 406 along a periphery of the glenoid 404. Light bleeding can be caused at the bone bed 402 which can promote a healing response. Other techniques known to those skilled in the art for promoting a healing response can also be utilized, such as using agents or stimulators that promote bone or tissue healing (e.g., platelet-rich plasma or erythropoietin).

As shown in FIG. 5, one or more suture anchors can be inserted into the bone bed 402. For example, a first suture anchor 408 and a second suture anchor 410 can be placed in the bone bed 402 and inserted near a rim of the glenoid 404. In some embodiments, the first suture anchor 408 and the second suture anchor 410 can be placed just behind the labrum 406. A placement of the one or more suture anchors 408, 410 can be based on factors such as patient anatomy, dimensions of a bone barrier, and a desired awning or lateral extension of the bone barrier with respect to the glenoid 404. While two suture anchors are illustrated in the embodiment of FIG. 5, a greater or fewer number of suture anchors (e.g., one, three, four, etc.) can be inserted into the bone bed 402, at least for the purpose of securing a bone barrier to the bone bed. The number of suture anchors used can be based on, for example, patient anatomy and dimensions of the bone barrier. By way of non-limiting example, exemplary suture anchors can include the GRYPHON® suture anchor, the GII® suture anchor, the MILAGRO® suture anchor, all of which are available from Mitek Sports Medicine of Raynham, Mass., as well as various forms of soft anchors, such as those disclosed in U.S. Pat. No. 9,345,567, the contents of which is incorporated herein by reference in its entirety. In the illustrated embodiment, the first suture anchor 408 includes a first suture 412 having a first suture limb 412*a* and a second suture limb 412*b* extending therefrom and the second suture anchor 410 includes a second suture 414 having a first suture limb 414*a* and a second suture limb 414*b* extending therefrom. In other embodiments, a single anchor can be multiply-loaded such that multiple sutures used in a repair are disposed on the same anchor (e.g. one anchor 408 can be double-loaded with the first and second sutures 412 and 414) and subsequently disposed within the bone at a location that allows the repair to be performed at opposed ends of the bone bed 402 (e.g., the locations where the suture limbs 412a, 412b and 414a, 414b extend from the bone bed 402 in FIG. 5).

FIG. 6 illustrates another step or action in an exemplary method of attaching and securing a bone barrier to the bone bed 402. More particularly, a suture limb of the suture of one or more suture anchors can be passed through or under the labrum 406. For example, a suture limb 412b of the first suture 412 can be passed under or through the labrum 406. Similarly, a suture limb 414b of the second suture 414 can be passed under or through the labrum 406. By way of non-limiting example, an exemplary suture can include a DYNACORD™ suture, PERMACORD™ suture, PER-MATAPE™ suture, or ORTHOCORD™ high strength orthopaedic suture, each of which is commercially available from Mitek Sports Medicine of Raynham, Mass.

Figures 7, 8, 9:
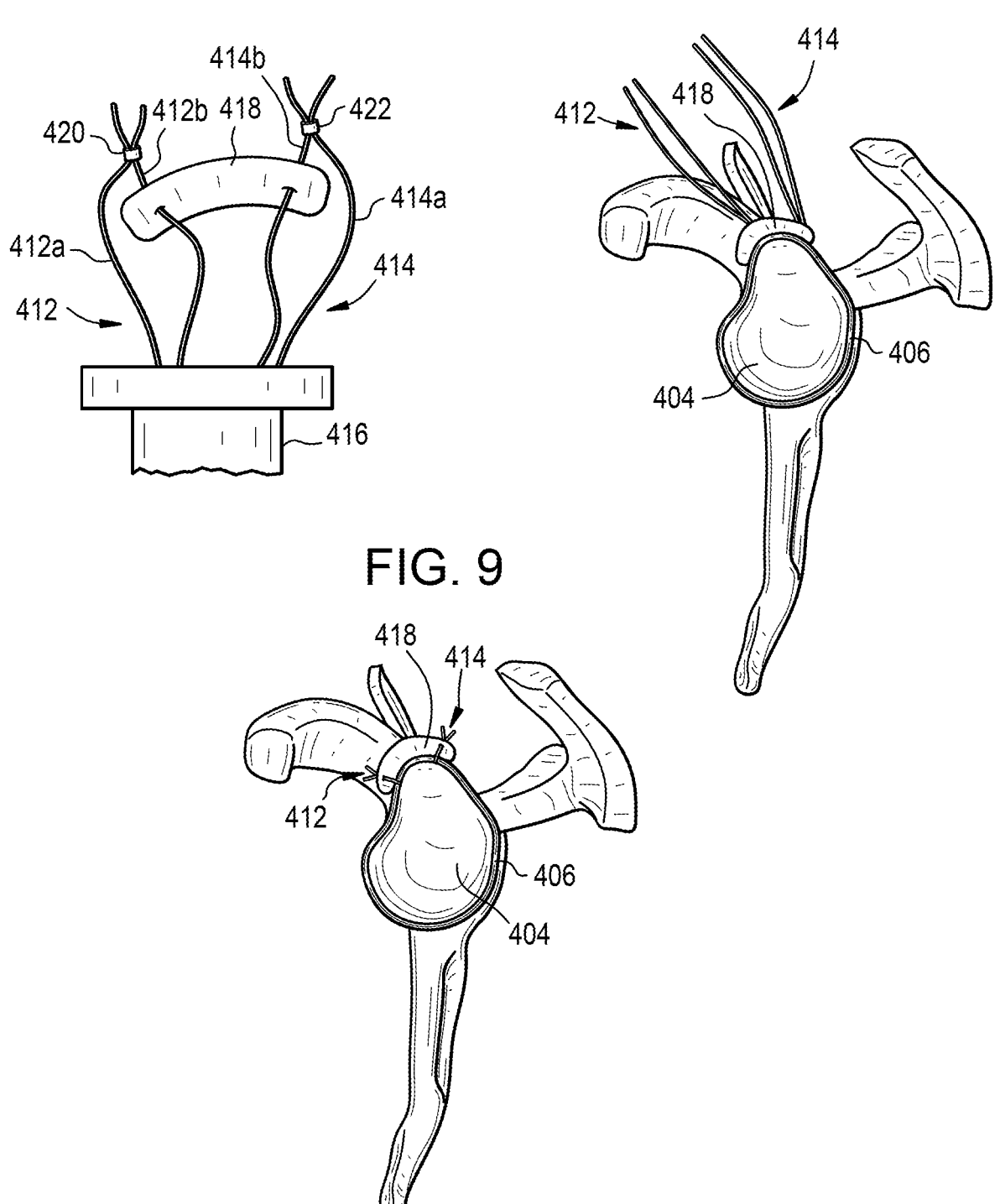
FIG. 7 is a front view of one exemplary embodiment of a bone barrier, the sutures of FIG. 5, and a cannula illustrating a fourth portion of the one exemplary method started in FIG. 4.
FIG. 8 is a front view of the shoulder joint of FIG. 4 illustrating a fifth portion of the one exemplary method started in FIG. 4.
FIG. 9 is a front view of the shoulder joint of FIG. 4 illustrating a sixth portion of the one exemplary method started in FIG. 4.

As shown in FIG. 7, the first and second limbs 412a, 412b of the first suture 412 and the first and second limbs 414a, 414b of the second suture 414 can be drawn through a cannula 416 to a position exterior to the surgical site, for example outside of a body (i.e., outside of the skin of the patient, which is the outside environment vis-à-vis the patient), or at least outside of the region within the body where the surgery is being performed but still underneath the skin from the perspective of the surgeon. With the suture limbs drawn through the cannula 416, a surgeon can manipulate and work with the suture limbs and a bone barrier 418 in an unobstructed manner. A suture limb from each suture 412, 414 can be passed through the bone barrier 418. For example, the second suture limb 412b of the first suture 412 and the second suture limb 414b of the second suture 414 can be passed through the bone barrier 418. A sliding knot can then be tied to connect the suture limb passing through the bone barrier 418 and a corresponding free suture limb of the suture. For example, a first sliding knot 420 can be tied in the first suture 412 connecting the first suture limb 412a and the second suture limb 412b. A second sliding knot 422 can be tied in the second suture 414 connecting the first suture limb 414a and the second suture limb 414b. The first sliding knot 420 and the second sliding knot 422 can be tied at a location proximal to the bone barrier 418. Exemplary, non-limiting sliding knots that can be used in the procedures provided for herein include a Buntline Hitch, a Tennessee Slider, a Duncan Loop, a Hangman's Noose, and a coaxial sliding neck.

The bone barrier 418 can then be moved towards or reduced to the bone bed 402, as shown in FIG. 8. Delivering the bone barrier 418 to the bone bed 402 can include passing the bone barrier 418 through the cannula 416 and reducing the bone barrier 418 to the bone bed 402 such that a distal-facing surface of the bone barrier 418 contacts the bone bed 402. A person skilled in the art will appreciate a number of different tools that can be utilized to advance the bone barrier 418 towards the bone bed 402, such as various forms of suture or knot pushers and other shafts having ends capable of contacting and/or reducing the bone barrier 418 towards the bone bed 402. The bone barrier 418 can be reduced to the bone bed 402 such that a portion of the bone barrier 418 extends laterally over the glenoid 404 to create an "awning" to the glenoid 404. Reduction of the bone barrier 418 to the bone bed 402 can result in a pre-determined extension of the bone barrier 418 over the glenoid 404. The pre-determined extension can be based on, at least in part, an anatomy of the patient such that the bone barrier can effectively oppose abnormal migration of a humeral head. In some embodiments, delivering the bone barrier 418 to the bone bed 402 can include arthroscopic delivery.

FIG. 9 illustrates the bone barrier 418 secured to the bone bed by the first suture 412 and the second suture 414 such that at least a portion of the distal-facing surface of the bone barrier is in contact with at least a portion of the bone bed 402 and a terminal end of the bone barrier 418 extends laterally over a terminal end of the bone bed. More particularly, after reducing the bone barrier 418 to the bone bed 402, the first sliding knot 420 and the second sliding knot 422 can be tightened to secure the bone barrier 418 in place with respect to the bone bed 402. In some embodiments, the sliding knots 420, 422 can be complemented with additional knots in one or more of the sutures 412, 414. For example, one or more half-hitches can be tied in one or more of the sutures 412, 414 to further secure the bone barrier 418 to the bone bed 402 and/or the location of the bone barrier 418 with respect to the bone bed 402. As can be seen in FIG. 9, the limbs of the first suture 412 and the limbs of the second suture 414 can be trimmed.

It will be appreciated that the above-described steps of an exemplary method are not limited to the order in which they are presented herein. For example, in some embodiments suture management can be accomplished in a different manner by modifying a sequence of tying one or more knots in a suture and reducing the bone barrier to the bone bed. More particularly, in some embodiments, a bone barrier can be reduced to the bone bed along one or more sutures. One or more knots can be tied in the one or more of the sutures after partially or fully reducing the bone barrier to the bone bed. In some embodiments, the bone barrier can be secured to the bone bed with one or more knotless anchoring devices or anchoring/securing means, including but not limited to various knotless sutures, suture constructs, suture systems, staples, screws and washers, etc. The term securing means as used herein can refer to any of the various systems and devices described herein for purposes of attaching the bone barrier to the glenoid.

Figure 10:
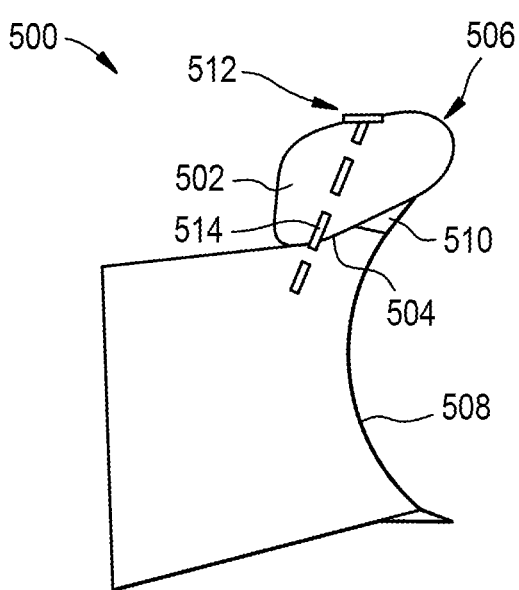
FIG. 10 is a schematic side view of a shoulder joint having a bone barrier located therein illustrating a portion of another exemplary method of implanting a bone barrier on a glenoid.

FIG. 10 shows an alternative embodiment of a method of placing and securing a bone barrier to a bone bed. A shoulder 500 is shown with a bone barrier 502 secured to a bone bed 504 such that an awning 506 of the bone barrier 502 can oppose abnormal motion of an adjacent bone (i.e., a humeral head). The awning 506 of the bone barrier 502 can extend over a glenoid 508 of the shoulder 500. As discussed above, a location of the bone bed 504, and, accordingly, a place-ment of the bone barrier 502, can be along a periphery of the glenoid 508 and can be adjacent to a labrum 510 of the glenoid 508. The bone barrier 502 can be secured to the bone bed 504 with at least one washer 512 and at least one screw 514. More particularly, as shown, the screw 514 can extend through the bone barrier 502 and into the bone bed 504. The washer 512 can be placed on a proximal-facing surface of the bone barrier 502. The washer 512 can aid in securing the bone barrier 502 and can distribute forces from the screw 514 more evenly across the bone barrier.

Figure 11:
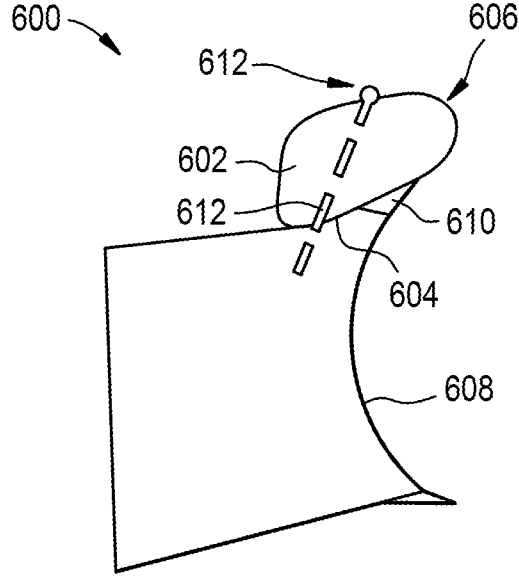
FIG. 11 is a schematic side view of a shoulder joint having a bone barrier located therein illustrating a portion of yet another exemplary method of implanting a bone barrier on a glenoid.

FIG. 11 shows yet another embodiment of a method of placing and securing a bone barrier to a bone bed. A shoulder 600 is shown with a bone barrier 602 secured to a bone bed 604 such that an awning 606 of the bone barrier 602 can oppose abnormal motion of an adjacent bone (i.e., a humeral head). The awning 606 of the bone barrier 602 can extend over a glenoid 608 of the shoulder 600. As discussed above, a location of the bone bed 604 and, accordingly, a placement of the bone barrier 602, can be along a periphery of the glenoid 608 and can be adjacent to a labrum 610 of the glenoid 608. The bone barrier 602 can be secured to the bone bed 604 with at least one staple 612. While a single staple 612 is illustrated in FIG. 11, one or more additional staples can be used to secure the bone barrier 602 to the bone bed 604 based on, for example, patient anatomy and a size of the bone barrier 602.

Figure 12:
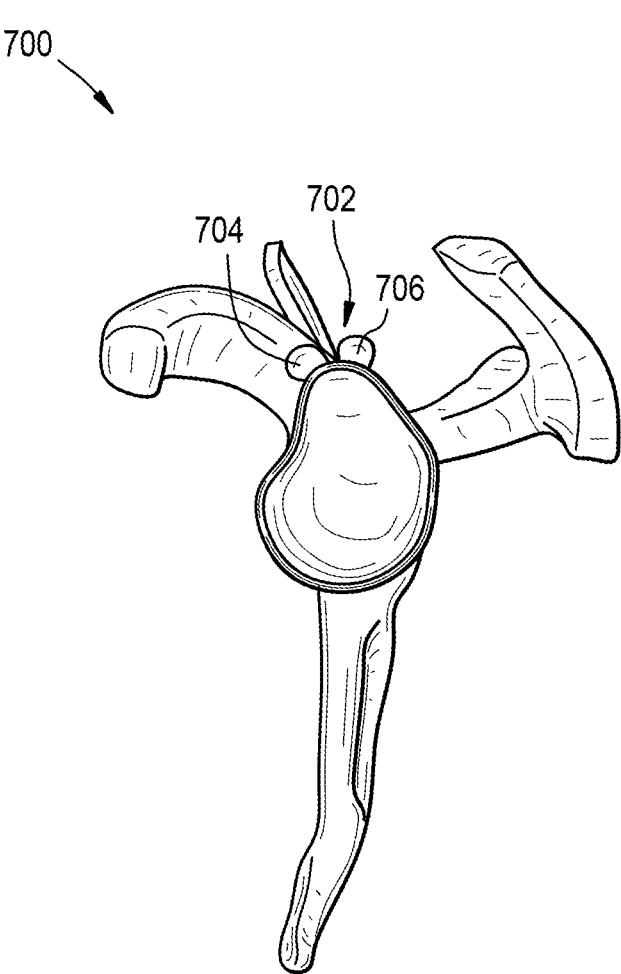
FIG. 12 is a front view of a shoulder joint having still another exemplary embodiment of a bone barrier implanted therein.

FIG. 12 illustrates another embodiment of a bone barrier. A shoulder 700 is shown with a bone barrier 702 secured to a bone bed such that the bone barrier can oppose abnormal motion of an adjacent bone (i.e., a humeral head). As shown, in the illustrated embodiment the bone barrier 702 includes a plurality of discrete bone barriers. For example, a first bone barrier piece 704 and a second bone barrier piece 706 can each be secured to a bone bed such that the first bone barrier piece and the second bone barrier piece together can oppose abnormal motion of the adjacent bone. While two discrete bone barrier pieces are illustrated in FIG. 12, one or more additional bone barrier pieces can be used in the bone barrier 702. The number of discrete bone barrier pieces can be a function of patient anatomy, including a size and/or magnitude of a defect or abnormal motion and dimensions of each of the discrete bone barrier pieces. Using a plurality of discrete bone barrier pieces to form a bone barrier of the present disclosure can be advantageous in instances in which there is a relatively big defect in patient anatomy and/or in which a magnitude of abnormal motion of an adjacent bone is large. Further, the use of a plurality of discrete bone barrier pieces can provide additional flexibility in allowing various geometries of an "awning" to be formed in the context of the present disclosure.

Any of the methods described above can be used to secure the first bone barrier piece 704 and the second bone barrier piece 706. In some embodiments, each of the plurality of discrete bone barrier pieces can be secured in the same manner, while in other embodiments, one or more of the plurality of discrete bone barrier pieces can be secured to a respective location on the bone bed in different ways. In some instances in which a plurality of discrete bone barrier pieces form a bone barrier 702, it can be desirable to independently implant and secure each bone barrier piece. For example, the first bone barrier piece 704 can be positioned and secured such that a distal-facing surface of the first bone barrier piece contacts a bone bed. The second bone barrier piece 706 can then be positioned and secured such that a distal-facing surface of the second bone barrier piece contacts a bone bed. In some embodiments, the first bone barrier piece 704 and the second bone barrier piece 706 can each be secured using at least one staple and/or at least one washer and screw, as described above. Securing each discrete bone barrier piece 704, 706 with a staple and/or a washer and screw can be particularly effective for independently implanting and securing each bone barrier piece. Independently implanting and securing each of the bone barrier pieces can reduce complexity of the procedure and can allow for more precise positioning of each of the plurality of bone barrier pieces relative to one another. In other embodiments, one or more of the discrete bone barrier pieces can be implanted and secured to a bone bed simultaneously.

Preferably, the various embodiments of a bone barrier(s) provided for herein can be delivered to a surgical site in sealed packaging in a sterilized manner. For example, the packaging can be a closed and sealed container, such as a plastic or TYVEK® bag. A person skilled in the art will recognize various ways by which sterilization can be achieved. The sealed container keeps the instrument sterile until it is opened in the medical facility. In instances in which the bone barrier(s) are formed at a surgical site, the packaging is typically less relevant, although it could be used, such as for shipping harvested allograft materials to another surgical site for use with another patient.

One skilled in the art will appreciate further features and advantages of the disclosure based on the above-described embodiments. Accordingly, the disclosure is not to be limited by what has been particularly shown and described, except as indicated by the appended claims. For example, to the extent the present disclosure discloses using the devices and methods provided for herein for opposing abnormal motion of a humeral head with respect to shoulder, a person skilled in the art will recognize how the present disclosure can be adapted for use with other anatomies. All publications and references cited herein are expressly incorporated herein by reference in their entirety.

What is claimed is:

1. A system for preventing abnormal humeral head migration in a shoulder, comprising:

a bone barrier having a terminal end that is configured to extend laterally beyond an upper periphery of a glenoid when the bone barrier is delivered to a bone bed at a location that is superior to the glenoid, the bone barrier including a strong, conforming material that conforms to a portion of the bone bed and to a portion of the glenoid adjacent to the bone bed, the bone barrier being dimensioned such that when the bone barrier is delivered to the bone bed it contacts an adjacent humeral head to maintain desired motion of the humeral head with respect to the glenoid and to prevent abnormal migration of the humeral head in a superior direction with respect to the glenoid; and one or more securing means for attaching the bone barrier to the bone bed at the location that is superior to the glenoid such that the terminal end of the bone barrier extends laterally beyond a terminal end of the bone bed to form an overhang over the glenoid with a distal facing surface of the bone barrier at least one of: being fixed relative to the bone bed or in contact with the bone bed at the upper periphery of the glenoid.

2. The system of claim 1, wherein the bone barrier is formed from a biological material suitable for long term placement within a body.

3. The system of claim 1, wherein the bone barrier comprises a synthetic material.

4. The system of claim 1, wherein the bone barrier comprises a fibrous tissue.

5. The system of claim 1, wherein the bone barrier comprises two or more distinct materials.

6. The system of claim 1, wherein the bone barrier comprises two or more discrete buffer pieces.

7. The system of claim 1, wherein the securing means includes at least one suture anchor and at least one suture.

8. The system of claim 1, wherein the securing means includes at least one screw and at least one washer.

9. The system of claim 1, wherein the securing means includes at least one staple.

10. The system of claim 1, wherein a surface of the bone barrier that is configured to contact the bone bed and extend laterally beyond the terminal end of the bone bed has a surface area approximately in the range of about 50 millimeters$^2$ to about 1000 millimeters$^2$.

11. The system of claim 10, wherein a thickness of the bone barrier is approximately in the range of about 1 millimeter to about 20 millimeters.

12. The system of claim 5, wherein the bone barrier comprises a stiff core of a first material covered by a second compliant surface material.

13. The system of claim 8, wherein the washer is sized to distribute forces evenly across the bone barrier.

14. The system of claim 7, wherein the at least one suture anchor is configured to be implanted into the bone bed and the at least one suture includes two suture tails extending from the suture anchor and the bone bed.

15. The system of claim 7, wherein the at least one suture includes two suture tails and at least one of the two suture tails is configured to be passed through a labrum.

16. The system of claim 7, wherein the at least one suture includes two suture tails and at least one of the two suture tails is configured to be passed under a labrum.

17. The system of claim 14, wherein a first suture tail of the two suture tails is configured to be passed through the bone barrier and a second suture tail of the two suture tails is configured to extend from the suture anchor and is coupled to the first suture tail with a sliding knot.

\* \* \* \* \*